United States Patent [19]

Repta et al.

[11] Patent Number: 4,684,630

[45] Date of Patent: Aug. 4, 1987

[54] METHOD OF PARENTERALLY DELIVERING DRUGS AND RELATED COMPOSITIONS

[76] Inventors: Arnold J. Repta, Rte. 6, P.O. Box 100N; Parviz Mojaverian, 105-WW Waldon Ct., both of Lawrence, Kans. 66044

[21] Appl. No.: 720,035

[22] Filed: Apr. 4, 1985

Related U.S. Application Data

[63] Continuation of Ser. No. 526,104, Aug. 24, 1983, abandoned.

[51] Int. Cl.$^4$ .................... A61K 31/70; C07H 17/00
[52] U.S. Cl. .................................. 514/49; 514/936; 536/23
[58] Field of Search ................ 536/23; 514/49, 936

[56] References Cited

U.S. PATENT DOCUMENTS

| Re. 28,819 | 5/1976 | Thompson | 424/243 |
|---|---|---|---|
| 3,070,502 | 12/1962 | Sponnoble | 424/227 |
| 3,472,931 | 10/1969 | Stoughton | 424/180 |
| 3,551,554 | 12/1970 | Herschler | 424/7 |
| 3,833,725 | 9/1974 | Thompson | 424/243 |
| 3,998,807 | 12/1976 | Moffatt | 536/23 |
| 4,069,382 | 1/1978 | Baker et al. | 536/26 |
| 4,330,534 | 5/1982 | Sakurai et al. | 536/23 |
| 4,405,611 | 9/1983 | Chatterji et al. | 536/23 |

OTHER PUBLICATIONS

Washington, Influences of Parenterally Administered Dimethyl Sulfoxide on Regional Blood Flow, Chem. Abstracts 83:173190d (1974).
Somogyi et al., Dimethyl Sulfoxide (DMSo), A Convenient Solvent of 7,12-Dimethylbenz(9)anthracene for Intravenous Injection, Chem. Abs. 73:69800k (1970).
Ladage et al., Solvent Vehicle for Therapeutics and Pharmaceutical Composition Containing H, Chem. Abstracts 92(2): 11236g (1979).
Haughey et al., Stabilized Oxytetracycline Solutions for Parenteral Administration, Chem. Abstracts 89: 220881r (1978).
Chatterji et al., "Stabilization of 5-Azacytidine by Nucleophilic Addition of Bisulfite Ion," *Journal of Pharmaceutical Sciences,* 66(7): 822–826 (1979).
Notari et al., "Kinetics and Mechanisms of Degradation of the Antileukemic Agent 5-Azacytidine in Aqueous Solutions," *Journal of Pharmaceutical Sciences,* 64(7): 1148–1157 (1975).
Chatterji, "Stability of Azacytidine in Infusion Solutions: Clarification of Conflicting Literature Data," *American Journal of Hospital Pharmacy,* 39:1638, 1640 (Oct. 1982).
Beisler et al., "Synthesis and Antitumor Activity of 5-Azacytosine Arabinoside," *J. Med. Chem.,* 22:1230–34 (1979), p. 2.
Benjamin et al., "Degradation Mechanism for 5-Azacytidine and Related Compounds in Aqueous Media," *Amer. Pharm. Assn.,* 11:60 (1981), Abstract No. 16, p. 2.
Benjamin, "The Chemistry of the Degradation of 5-Azacytidine and Some Derivatives of 5-Azacytosine," Doctoral Dissertation, The University of Kansas, 1979, pp. 2, 3.
Beisler, "Isolation, Characterization, and Properties of a Facile Hydrolysis Product of the Antitumor Nucleoside, 5-Azacytidine," *J. Med. Chem.,* 21:204–208 (1978), p. 3.
Mojaverian et al., "Development of an Intravenous Formulation or the Unstable Investigational Cytotoxic Nucleosides 5-Azacytosine Arabinoside (NSC 281272) and 5-Azacytidine (NSC 102816)," *J. Pharm. Pharmacol.,* 36:728–733 (1984).

*Primary Examiner*—Johnnie R. Brown
*Assistant Examiner*—John W. Rollins
*Attorney, Agent, or Firm*—Allegretti, Newitt, Witcoff & McAndrews, Ltd.

[57] ABSTRACT

A method of parenterally delivering aqueously unstable drugs that includes the aqueous dilution of a stable, anhydrous organic solution having the drug dissolved therein. The resulting organic-aqueous solution is physiologically suitable for parenteral delivery into a warm-blooded mammal and contains the drug in an effective dosage concentration per unit volume.

2 Claims, No Drawings

METHOD OF PARENTERALLY DELIVERING DRUGS AND RELATED COMPOSITIONS

This is a continuation of copending application Ser. No. 526,104, filed Aug. 24, 1983, now abandoned.

BACKGROUND OF THE INVENTION

1. Field of the Invention

The present invention relates to methods for parenterally delivering drugs that are unstable in aqueous media and also to compositions useful in delivering such drugs.

2. Description of the Prior Art

Intravenous techniques are the principal means of parenterally delivering drugs to humans. The delivery vehicles used in connection with such techniques are physiologically compatible aqueous solutions, such as dextrose or saline solutions. While aqueous solutions provide adequate parenteral delivery vehicles for many drugs, there are some drugs that are unstable in such aqueous media and degrade therein to useless or harmful byproducts. Some of these aqueously unstable drugs can be administered parenterally by use of a prodrug or a drug stabilizer. However, there is a remaining class of drugs that cannot be adequately stabilized in aqueous media suitable for parenteral infusion. Such drugs present serious problems in handling, storage, and delivery and are not administered parenterally, though this is often the most preferable means of delivering a drug.

Two examples of drugs that are unstable in aqueous media and, therefore, hitherto unsuitable for parenteral delivery are 5-azacytosine arabinoside (hereinafter ara-AC) and 5-azacytidine (hereinafter 5-AC), the latter also being known as 5-azacytosine riboside. Both of these drugs are promising anticancer agents. Beisler et al., "Synthesis and Antitumor Activity of 5-Azacytosine Arabinoside," *J. Med. Chem.*, 22: 1230-34 (1979). Studies have clearly indicated, however, that 5-AC degrades at a relatively rapid rate in aqueous solutions. Benjamin et al, "Degradation Mechanism for 5-Azacytidine and Related Compounds in Aqueous Media," *Amer. Pharm. Assn.*, 11: 60 (1981), Abstract No. 16; Benjamin, "The Chemistry of the Degradation of 5-Azacytidine and some Derivatives of 5-Azacytosine," Doctoral Dissertation, The University of Kansas, 1979. Additional studies by the inventors that are not in the prior art show ara-AC undergoes a similar degradation process. For example, ara-AC shows 10% decomposition in water in a period of 1.8 hours at 25° C. ($t_{90}=1.8$ hours). Such a rapid rate of decomposition make it impossible to manufacture and store aqueous solutions of these anticancer agents. Furthermore, this rapid degradation rate makes it very difficult if not impossible to administer an aqueous solution of 5-AC or ara-AC intravenously over a normal period of 12-24 hours. It appears that this stability problem cannot be solved by the use of stabilizers or prodrugs. Id. This led one researcher to conclude that prolonged purely aqueous intravenous infusion was the only way to clinically administer 5-AC, despite the obvious disadvantages presented by its facile decomposition into products of unknown toxicity. Beisler, "Isolation, Characterization and Properties of a Facile Hydrolysis Product of the Antitumor Nucleoside, 5-Azacytidine," *J. Med. Chem.*, 21: 204-208 (1978).

Therefore, there is a need for a method for parenterally delivering drugs that are aqueously unstable such that the drug composition has commercially adequate storage life and yet can be made physiologically compatible for parental infusion.

SUMMARY OF THE INVENTION

It is an object of the present invention to provide a method for parenterally delivering drugs that are unstable in aqueous media into warm-blooded mammals with a minimum amount of aqueous degradation of the drugs.

It is another object of the present invention to provide compositions containing drugs that are unstable in aqueous media that nonetheless possess adequate storage life for commercial production and distribution and yet are physiologically compatible such that they can be used in connection with the parenteral administration of the drug.

It is a specific object of the present invention to provide a method for parenterally delivering an aqueously unstable drug into a warm-blooded mammal whereby a stable, anhydrous organic solution that includes the drug dissolved in a highly water soluble organic solvent is diluted with water or some other aqueous solution to form an organic-aqueous solution. The drug is stable in the anhydrous solution because no water is present. This initial organic solution, therefore, exhibits good storage and handling life with no aqueous decomposition of the drug. Prior to delivery, the organic solution is diluted to form an organic-aqueous solution that is physiologically suitable for parenteral delivery into the warm-blooded mammal. In other words, the organic solution must be made aqueous enough such that it can be safely introduced parenterally. Furthermore, the diluted organic-aqueous solution must contain the drug in an effective dosage concentration per unit volume of the organic-aqueous solution. Preferably, the dilution of the stable, organic solution takes place immediately prior to the parenteral introduction into the body. This minimizes the time to which the drug is exposed to aqueous decomposition outside the body.

It is a further specific object of the present invention to provide stable, anhydrous, organic solutions comprising an aqueously unstable drug dissolved in a highly water soluble solvent as described above.

Additional objects and embodiments of the present invention will be made clear in the following description of the preferred embodiments and claims.

DESCRIPTION OF THE PREFERRED EMBODIMENTS

The present invention may be utilized with a variety of chemically dissimilar drugs that are unstable in aqueous media. However, not all water miscible solvents may be used with all drugs. The determination of which organic solvents may be used with which aqueous diluting solutions with respect to a particular drug is primarily a matter of comparing the relative solubilities of the particular drug in the two solutions. First, the drug should preferably be sufficiently soluble in the organic solvent such that even upon substantial aqueous dilution, the resulting organic-aqueous solution will still contain the drug in an effective dose concentration per unit volume of the organic-aqueous solution. Second, the drug should preferably be sufficiently soluble in the aqueous diluting solution such that the drug does not precipitate out of the organic-aqueous solution to any significant degree upon dilution. Significant precipitation may render the organic-aqueous solution physiologically unsuitable for parenteral injection due to the presence of crystals that could cause thrombosis. Also, significant precipitation may result in a drug concentration below the effective dosage per unit volume for the drug. A third concentration is the compatibility of the organic solvent and the aqueous solution. The organic solvent should be miscible or at least highly soluble in the aqueous solution. Additionally, the solubility of the drug in the organic solvent must not be excessively greater than the solubility of the drug in the aqueous diluting solution. If there is a marked difference between the two solubilities, it is possible that undesirable precipitation may accompany the dilution process. This may be true even though no precipitation would occur in the resulting organic-aqueous solution at equilibrium.

The physiological compatibility of the resulting organic-aqueous solution is also a factor in selecting an appropriate organic solvent. Some organic solvents may be so highly toxic that no amount of aqueous dilution could render the organic drug solution physiologically suitable for parenteral delivery without also reducing the drug's concentration per unit volume well below the effective dosage. However, many solvents that are toxic in undiluted form may be safely administered when diluted and yet have enough solvent power to accept an effective drug dosage per unit volume. Examples of water miscible organic solvents that may be appropriate with various aqueously unstable drugs are dimethylsulfoxide (DMSO), dimethylacetamide (DMA), dimethylformamide, ethanol, various alcohols, glycols, glycerine, propylene glycol, and various polyethylene glycols.

A further consideration in the selection of an organic solvent is its compatibility with commercial intravenous injection equipment. For example, an anhydrous DMSO or DMA solution will dissolve many commercial plastics that are currently used for intravenous delivery tubes. In the case of DMSO, this problem can be avoided by diluting the organic solution in two steps. The stable, anhydrous DMSO or DMA solution containing the drug to be administered can first be diluted with water or another aqueous media to a DMSO or DMA concentration of below about 90%, preferably 70%, based on the total weight of the resulting organic-aqueous solution. It has been shown that diluted DMSO and DMA solutions of less than 90% concentration do not adversely affect many commercial plastics and do not extract their plasticizers. These diluted solutions could then be safely used in connection with standard intravenous equipment and further diluted to a physiologically compatible concentration level immediately prior to delivery, as discussed below.

The aqueous diluting solutions that are preferred for use with the present invention are standard intravenous or parenteral aqueous delivery vehicles, such as dextrose solutions, saline solutions, or dextrose-saline solutions. Other aqueous solutions may be used so long as they result in an organic-aqueous solution that is physiologically suitable for parenteral administration and contains an effective dosage concentration per unit volume.

The present invention will be further described below using as examples the two anticancer agents, 5-AC and ara-AC. However, it is to be understood that the present invention has application to any aqueously unstable drug that can be stabilized in an anhydrous organic solution that can in turn be aqueously diluted to yield a parenterally deliverable organic-aqueous solution that is physiologically compatible and pharmacologically effective.

EXAMPLE 1

Two neat, anhydrous solutions of ara-AC dissolved in DMSO and DMA, respectively, were prepared. Ara-AC showed a solubility of 370 mg/ml in DMSO and 170 mg/ml in DMA. Ara-AC has a solubility of approximately 20 mg/ml in water. The effective dose for ara-AC is 700 mg. The ara-AC in the two resulting organic solutions was found to have undergone no observable degradation during 5 months at ambient temperatures (6° C. and 25° C.). At higher temperatures (e.g., 50°–60° C.), the ara-AC has proven stable for at least 3 weeks. Thus, the solutions of ara-AC in DMSO and DMA appear to be stable enough for commercial production, handling, and storage. By contrast, a solution of ara-AC in water would degrade 10% in 1.8 hours at 25° C.

EXAMPLE 2

Example 1 is repeated using 5-AC in place of ara-AC. Similar stability results are obtained.

EXAMPLE 3

The DMSO solution of Example 1 was diluted to a 70 wt % DMSO-30% wt. % water solution. The DMA solution of Example 1 was diluted to a 65 wt. % DMA-35 wt. % water solution. Both of these solutions were compatible with most known commercial intravenous injection equipment. Furthermore, these organic-aqueous solutions had $t_{90}$ values of 28.0 and 16.0 hours, respectively. Since an intravenous infusion usually lasts no longer than 12–24 hours, the enhanced stability of these organic-aqueous solutions vis-a-vis entirely aqueous solutions makes it practical to dilute the neat, anhydrous organic solvents prior to the beginning of intravenous infusion without any substantial loss of the drug due to aqueous degradation. Table I shows the stability characteristics of ara-AC in various solvent systems.

The degradation kinetics shown in Table I were studied at 25° C. using a reverse phase HPLC system consisting of a $C_{18}$ μ-Bondapak column, phosphate buffer (0.01M, pH 6.8) as the mobile phase (flow rate adjusted to 2.0 ml/min) and a uv detector at 254 nm. Drug concentrations of 5 mg/ml were properly diluted in water, along with the internal standard (Uracil, 0.6 mg/ml), chromatographed, and quantitated (at 0.05 or 0.10 detector attenuation). Sample aliquots of 5 μl were injected. In aqueous media the internal standard, the degradation product, and the parent ara-AC were eluted with retention volumes of 9.0 ml, 13 ml, and 17 ml, respectively. Degradation of ara-AC was followed qualitatively and quantitatively (by use of a standard curve) in each experiment. Both the DMA and DMSO used were of spectrophotometric grade and water free. The pH of the drug solution in purely aqueous solution and in mixed solvent systems was measured several times throughout the study and appeared to remain constant.

TABLE I

Stability Characteristics of Ara-AC
At 25° C. in Various Solvent Systems

| Medium | [I] mg/ml | Measured pH of the Solution[a] | $t_{90}$ (hr.) | $K_{obs}$ (hr.$^{-1}$) |
|---|---|---|---|---|
| Distilled $H_2O$ | 0.25 | 6.8 | 1.8 | $1.34 \times 10^{-2}$ |
| Buffer[c] | 0.25 | 7.0 | 1.7 | $1.55 \times 10^{-2}$ |
| 5% DMSO in Buffer[d] | 5.0 | 7.0 | 2.0 | $4.67 \times 10^{-2e}$ |

TABLE I-continued

Stability Characteristics of Ara-AC
At 25° C. in Various Solvent Systems

| Medium | [I] mg/ml | Measured pH of the Solution[a] | $t_{90}$ (hr.) | $K_{obs}$ (hr.$^{-1}$) |
|---|---|---|---|---|
| 10% DMSO in Buffer | 5.0 | 7.1 | 2.5 | $3.82 \times 10^{-2}$[e] |
| 25% DMSO in Buffer | 5.0 | 7.4 | 2.8 | $2.80 \times 10^{-2}$[e] |
| 5% DMA in Buffer[d] | 5.0 | 7.0 | 1.9 | $4.17 \times 10^{-2}$[e] |
| 10% DMA in Buffer[d] | 5.0 | 7.1 | 2.2 | $3.90 \times 10^{-2}$[e] |
| 25% DMA in Buffer[d] | 5.0 | 7.4 | 2.7 | $2.89 \times 10^{-2}$[e] |
| 50% DMA in Buffer[d] | 5.0 | 8.1 | 4.5 | $2.13 \times 10^{-2}$[e] |
| 55% DMA in Buffer[d] | 5.0 | 8.3 | 6.0 | $1.55 \times 10^{-2}$[e] |
| 60% DMA in Buffer[f] | 5.0 | 7.4 | 15.0 | $7.3 \times 10^{-3}$[e] |
| 60% DMSO in Buffer[f] | 5.0 | 7.8 | 16.0 | $6.7 \times 10^{-3}$[e] |
| 70% DMSO in H$_2$O | 5.0 | 8.0 | 28.0 | $3.36 \times 10^{-3}$[e] |

[a]In mixed aqueous-organic system, the value represent apparent pH of the final mixture.
[b]Observed degradation rate constant was calculated from the equation
$K_{obs} = k_1 \frac{k_3}{k_2}$ which was derived from general degradation profile:

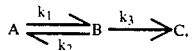

considering the steady state approximation(d[B]/dt = 0).
[c]Phosphate buffer, 0.01 M, pH 7.0, $\mu$ = 0.1 with NaCl.
[d]Phosphate buffer, 0.01 M, pH 6.8, $\mu$ = 0.1 with NaCl.
[e]First order degradation rate constant calculated from slope of the log concentration vs. time plot using the first six data points.
[f]Phosphate buffer, 0.03 M, pH 6.0, $\mu$ = 0.3 M with NaCl.

EXAMPLE 4

The procedure of Example 3 is repeated using 5-AC in place of ara-AC. Similar results are obtained.

EXAMPLE 5

The organic-aqueous solutions of Example 3 are further diluted with two standard sterile intravenous solutions: a 5% dextrose-0.45% saline solution and a 0.9% saline solution. The aqueous delivery vehicles were delivered at a rate of 250 ml/hr. The concentrated drug solutions (approx. 10 mg/ml) were introduced through a side arm tubing located several inches above the injection point for 12 hours at the rate of 6 ml/hr. measured by a calibrated infusion pump. Thus, during the 12 hour period, approximately 700 mg of ara-AC and 5-AC, respectively, were delivered. At this rate, the effective dosage concentration per unit volume of the final organic-aqueous solution was approximately 1 mg/ml. The final diluted organic-aqueous solutions were filtered using Wattman filter paper. No precipitation or other undesirable effects were noted.

The dilution step can be accomplished in any suitable manner. The most preferred method, i.e., "piggybacking" the concentrated drug solution into an intravenous delivery tube, is described above. Preferably, the drug solution should enter the stream of the aqueous vehicle at the latest possible point before infusion to minimize the degrading effect of the aqueous media upon the drug.

EXAMPLE 6

The neat, anhydrous solutions of Example 1 are placed in intravenous equipment made of materials resistant to DMSO and DMA (e.g., glass). The anhydrous solutions are separately piggybacked into separate streams of an aqueous parenteral delivery vehicle such that dilute organic-aqueous solutions are formed having less than about 5% organic solvent by weight. The resulting dilute organic-aqueous solutions are physiologically suitable for parental injection into humans and contain ara-AC in concentrations equal to an effective dosage per unit volume for the infusion time.

It is to be understood that the foregoing specification emphasizes certain objects and embodiments. However, the present invention is not limited by these specifics. All methods and compositions that fall within the spirit of the following claims are to be included within the scope of the present invention.

We hereby claim:

1. A method of intravenously injecting an aqueous unstable anticancer agent into a warm-blooded mammal, the agent being selected from the group consisting of 5-azacytosine arabinoside and 5-azacytidine, comprising in combination the following steps:
   (a) aqueously diluting a stable, anhydrous organic solution to form an organic-aqueous solution, the organic solution consisting of the agent and a highly water soluble organic solvent selected from the group consisting of dimethylsulfoxide and dimethylacetamide, the organic-aqueous solution having the organic solvent present in a concentration of less than about 5% based on the total weight of the organic-aqueous solution, the organic-aqueous solution being physiologically suitable for intravenous injection into the warm-blooded mammal, the agent being present in the organic-aqueous solution in an effective dosage concentration per unit volume of approximately 1 mg./ml.; and
   (b) intravenously injecting the organic-aqueous solution into the warm-blooded mammal;
the dilution step occuring immediately prior to the intravenous injection step.

2. A method of intravenously injecting an aqueously unstable anticancer agent into a warm-blooded mammal, the agent being selected from the group consisting of 5-azacytosine arabinoside and 5-azacytidine, comprising in combination the following steps:
   (a) aqueously diluting a stable, anhydrous organic solution to form a first organic-aqueous solution, the organic solution consisting of the agent and a highly water soluble organic solvent selected from the group consisting of dimethylsulfoxide and dimethylacetamide, the first organic-aqueous solution having the organic solvent present in a concentration of below about 90% based on the total weight of the first organic-aqueous solution;
   (b) aqueously diluting the first organic-aqueous solution to form a second organic-aqueous solution, the second organic-aqueous solution having the organic solvent present in a concentration of less than about 5% based on the total weight of the second organic-aqueous solution, the second organic-aqueous solution being physiologically suitable for intravenous injection into the warm-blooded mammal, the agent being present in the second organic-aqueous solution in an effective dosage concentration per unit volume of approximately 1 mg./ml.; and
   (c) intravenously injecting the second organic-aqueous solution into the warm-blooded mammal;
the dilution step (a) occurring less than or equal to approximately 24 hours prior to the intravenous injection step and the dilution step (b) occurring immediately prior to the intravenous injection step.

* * * * *